(12) United States Patent
Tanaka

(10) Patent No.: US 8,852,515 B2
(45) Date of Patent: Oct. 7, 2014

(54) MULTILAYER ANALYSIS ELEMENT FOR ANALYZING LIQUID SAMPLES

(75) Inventor: Hideaki Tanaka, Asaka (JP)

(73) Assignee: FUJIFILM Corporation, Tokyo (JP)

( * ) Notice: Subject to any disclaimer, the term of this patent is extended or adjusted under 35 U.S.C. 154(b) by 1450 days.

(21) Appl. No.: 11/661,786

(22) PCT Filed: Jul. 11, 2005

(86) PCT No.: PCT/JP2005/012782
§ 371 (c)(1),
(2), (4) Date: Mar. 1, 2007

(87) PCT Pub. No.: WO2006/030579
PCT Pub. Date: Mar. 23, 2006

(65) Prior Publication Data
US 2007/0258860 A1    Nov. 8, 2007

(30) Foreign Application Priority Data
Sep. 17, 2004 (JP) .................. 2004-271352

(51) Int. Cl.
*G01N 21/75* (2006.01)
*G01N 31/22* (2006.01)
*G01N 21/78* (2006.01)
G01N 33/48 (2006.01)
G01N 33/487 (2006.01)
G01N 33/497 (2006.01)

(52) U.S. Cl.
CPC ............. *G01N 31/22* (2013.01); *G01N 31/223* (2013.01); *G01N 33/48* (2013.01); *G01N 33/487* (2013.01); *G01N 33/497* (2013.01); *G01N 21/783* (2013.01)
USPC ............. 422/86; 422/420; 422/423; 422/428; 422/430; 422/68.1; 422/83; 436/164; 436/170

(58) Field of Classification Search
CPC .............................. G01N 31/22; G01N 31/223
USPC .......... 422/420, 423, 425, 428, 430, 68.1, 83, 422/86; 436/164, 170
See application file for complete search history.

(56) References Cited

U.S. PATENT DOCUMENTS

| | | | | |
|---|---|---|---|---|
| 3,024,701 A | * | 3/1962 | Marks et al. | 359/485.03 |
| 3,644,245 A | * | 2/1972 | Flanagan et al. | 524/262 |
| 4,066,403 A | | 1/1978 | Bruschi | |
| 4,444,839 A | * | 4/1984 | Dudzik et al. | 428/336 |
| 4,548,906 A | | 10/1985 | Sekikawa et al. | |
| 5,198,335 A | * | 3/1993 | Sekikawa et al. | 435/4 |
| 5,286,624 A | * | 2/1994 | Terashima et al. | 435/12 |
| 2002/0068364 A1 | | 6/2002 | Arai et al. | |

FOREIGN PATENT DOCUMENTS

| | | |
|---|---|---|
| JP | 52-3488 A | 1/1977 |
| JP | 58-77661 A | 5/1983 |
| JP | 4-157363 A | 5/1992 |
| JP | 4-157364 A | 5/1992 |
| JP | 6-222050 A | 8/1994 |
| JP | 2002-122585 A | 4/2002 |

OTHER PUBLICATIONS

Extended European Search Report dated Jul. 23, 2010 for corresponding European Application No. 05757806.4.

* cited by examiner

*Primary Examiner* — Lyle Alexander
(74) *Attorney, Agent, or Firm* — Birch, Stewart, Kolasch & Birch, LLP

(57) ABSTRACT

The problem is to provide a multilayer analysis element for analyzing liquid samples, having improved adhesive force between a transparent support and a detection layer even by handling at the time of processing, while maintaining basic performances such as sensitivity and storage performance. The multilayer analysis element for analyzing liquid samples is characterized in that at least a detection layer containing a substance that generates a detectable change by a gaseous substance, a liquid blocking layer that selectively permeates the gaseous substance, and a spreading layer are integrally adhesion laminated in this order on a transparent support, and the detection layer contains an adhesive polymer and a water-insoluble vinyl polymer.

1 Claim, No Drawings

MULTILAYER ANALYSIS ELEMENT FOR ANALYZING LIQUID SAMPLES

TECHNICAL FIELD

The present invention relates to a multilayer analysis element for analyzing liquid samples. More particularly, it relates to a multilayer analysis element for analyzing liquid samples for analyzing ammonia or an ammonia product such as creatine and urea in a liquid sample such as blood and urine.

BACKGROUND ART

Conventionally, as a measurement method of urea nitrogen in a body fluid, a method called a dry method (dry chemistry) has variously been proposed to attempt simplification and acceleration of measurement and to eliminate individual difference of a measurer. The typical method is to use an integral multilayer analysis element comprising a reagent layer containing urease and an alkaline buffer, an indicator layer that detects gaseous ammonia, and a permselective layer that selectively permeates only the gaseous ammonia, interposed between those. For example, Patent Document (JP-A-52-3488) discloses an integral analysis element basically having the above-described multilayer structure. This analysis element uses a hydrophobic polymer thin film as a permselective layer of an ammonia gas.

Patent Document 2 (JP-A-58-77661) discloses an integral multilayer analysis material for analyzing ammonia or an ammonia formation substrate in a liquid sample, comprising a transparent support having an indicator layer for gaseous ammonia, a liquid blocking layer, a reagent layer containing an alkaline buffer and if necessary a reagent that can product ammonia by reacting with a substrate, and a spreading layer, integrally adhesion laminated thereon in this order, characterized in that the liquid blocking layer comprises a porous substance, and constitutes air holes that substantially block a liquid sample and permeates a gaseous ammonia under use conditions. In this multilayer analysis material, an integral multilayer analysis element that uses a membrane filter as a permselective layer to improve adhesion to the indicator layer and to attempt sensitization is disclosed.

Besides, Patent Document 3 (JP-A-4-157363) discloses an integral multilayer analysis element for analyzing ammonia or an ammonia product, having further increased color optical density, low color optical density of background and further high measurement accuracy using a polyvinyl alkyl ether that does not substantially contain ammonia or ammonium ions in an undercoat layer of a support, or using a polyvinyl alkyl ether in a binder of an indicator layer. Further, Patent Document 4 (JP-A-4-157364) discloses an integral multilayer analysis element for analyzing ammonia or an ammonia product, having further increased color optical density, low color optical density of background and further high measurement accuracy by containing poly(N-vinylpyrrolidone) in a porous spreading layer, not substantially containing ammonia in an ammonia formation reaction reagent layer, and using a binder that does not generate ammonia at pH of about 9.0 or higher and does not change binder performance. Further, Patent Document 5 (JP-A-2002-122585) discloses an integral multilayer analysis element for analyzing ammonia or an ammonia product in a liquid sample, comprising a transparent support having an indicator layer containing a reagent that generates a detectable change by gaseous ammonia, a liquid blocking layer that passes gaseous ammonia, a reagent layer containing an alkali buffer and if necessary a reagent that can produce ammonia by reacting with a substrate, and a spreading layer, integrally adhesion laminated thereon in this order, characterized in that the liquid blocking layer comprises at least two layers of porous films.

Patent Document 1: JP-A-52-3488
Patent Document 2: JP-A-58-77661
Patent Document 3: JP-A-4-157363
Patent Document 4: JP-A-4-157364
Patent Document 5: JP-A-2002-122585

DISCLOSURE OF THE INVENTION

Problems that the Invention is to Solve

As described above, the integral multilayer analysis element for analyzing ammonia or an ammonia product disclosed in, for example, Patent Documents 2 to 5 is that an indicator layer containing a reagent that generates a detectable change by gaseous ammonia (a detection layer), a liquid blocking layer that passes gaseous ammonia, an ammonia formation reaction reagent layer, and a spreading layer are integrally adhesion laminated on a transparent support in this order, and if necessary, an overcoat layer containing a vinyl polymer is laminated on the spreading layer. Further, particularly in an integral multilayer analysis element for creatine determination, there is the case that an ammonia diffusion prevention layer and an endogenous ammonia complementary layer are further laminated between the ammonia formation reaction reagent layer and the spreading layer.

However, with repeating lamination of layers as described above, a component contained in the detection layer oozes in the liquid blocking layer which is a porous layer, adhesive force between the transparent support and the detection layer is decreased, there is the case of peeling by handling at the time of processing, and there was the problem that productivity does not rise.

Accordingly, an object of the present invention is to provide a multilayer analysis element for analyzing liquid samples, having improved adhesive force between a transparent support and a detection layer even by handling at the time of processing, while maintaining basic performances such as sensitivity and storage performance.

Means for Solving the Problems

The above problems can be solved by the following means.

1) A multilayer analysis element for analyzing liquid samples, which comprises a transparent support having at least: a detection layer containing a substance that generates a detectable change by a gaseous substance; a liquid blocking layer that selectively permeates the gaseous substance; and a spreading layer, integrally adhesion laminated thereon in this order, wherein the detection layer contains an adhesive polymer and a water-insoluble vinyl polymer.

2) The multilayer analysis element for analyzing liquid samples as described in 1) above, wherein the water-insoluble vinyl polymer has an acetal group.

3) The multilayer analysis element for analyzing liquid samples as described in 1) or 2) above, wherein the water-insoluble vinyl polymer is a polyvinyl butyral.

Advantage of the Invention

According to the present invention, because a specific polymer is contained in the detection layer, a multilayer analysis element for analyzing liquid samples, having improved adhesive force between a transparent support and a detection layer even by handling at the time of processing, while maintaining basic performances such as sensitivity and storage performance can be provided.

BEST MODE FOR CARRYING OUT THE INVENTION

The multilayer analysis element for analyzing liquid samples of the present invention is characterized by containing an adhesive polymer and a water-insoluble vinyl polymer in the detection layer containing a substance that generates a detectable change by a gaseous substance.

The substance that generates a detectable change by a gaseous substance in the present specification means a substance that as a result of reaction and/or interaction with a gaseous substance, structure changes and due to the change, change is generated in spectroscopic characteristics such as absorption wavelength. The "change of structure" used herein includes change of structure such as change of atomic composition, change of bonding relationship such as covalent bond and hydrogen bond, change of steric structure, and the like.

When the multilayer analysis element for analyzing liquid samples of the present invention has the structure comprising the transparent support having at least the detection layer, the liquid blocking layer, and the spreading layer, integrally adhesion laminated thereon in this order, at least one layer can be provided at one or more position selected from a position between the transparent support and the detection layer, a position between the detection layer and the liquid blocking layer, a position between the liquid blocking layer and the spreading layer, and a position on the spreading layer.

The multilayer analysis element for analyzing liquid samples of the present invention contains an adhesive polymer in the detection layer. The adhesive polymer is a polymer that contributes to adhesion of each of interfaces between the transparent support and the detection layer and between the detection layer and the liquid blocking layer.

It is preferable as the adhesive polymer used in the present invention that Tg is 0° C. or lower (more preferably from −150 to −5° C., and particularly preferably from −100 to −10° C.) Further, it is preferable that the adhesive polymer has a mass average molecular weight of from 10,000 to 1,000,000 (more preferably from 10,000 to 500,000, and particularly preferably from 20,000 to 200,000).

Examples of the adhesive polymer include a polyvinyl alkyl ether (such as a polyvinyl methylether, a polyvinyl ethyl ether and polyvinyl isobutyl ether), a natural rubber, chloroprene, a styrene butadiene rubber, a polymer mainly comprising an acrylic ester of an aliphatic alcohol having from 2 to 16 carbon atoms, and obtained by copolymerizing a small amount of a monomer having a polar group such as acrylic acid and acrylamide with the acrylic ester, a silicone pressure-sensitive adhesive constituted by a combination of a silicon rubber and a silicon resin, a pressure-sensitive adhesive mainly comprising a styrene-isoprene-styrene block polymer, a rosin resin, a terpene resin, a hydrogenated petroleum resin, a polyisobutylene, an indene, a dammar, a copal, a coumarone, a picopale, an alkyd resin, a cellulose ester and a neoprene. Of those, a polyvinyl alkyl ether is preferable.

Addition amount of the adhesive polymer is from 1 to 500 times, preferably from 3 to 300 times, and more preferably from 5 to 100 times, the amount of the indicator in the detection layer.

It is necessary that the water-insoluble vinyl polymer contained in the detection layer is insoluble in water, but it is preferable to be soluble in a coating solvent for detection layer formation, and it is further preferable to have compatibility with other polymer that can be used together. In the present specification, the term "insoluble in water" means that solubility in 100 g of water at 20° C. is 1 g or less. The detection layer coating solvent is generally an organic solvent or a mixed solvent of an organic solvent and water. The water-insoluble vinyl polymer is preferably soluble in an alcohol, and is particularly preferably ethanol-soluble.

Further, it is preferable as the water-insoluble vinyl polymer that Tg is 10° C. or higher (more preferably from 20 to 150° C., and particularly preferably from 30 to 120° C.). Further, the water-insoluble vinyl polymer is preferably that an average degree of polymerization is from 30 to 5,000 (more preferably from 50 to 3,000, and particularly preferably from 100 to 2,500).

It is preferable that the water-insoluble vinyl polymer has an acetal group. Examples of the acetal group include a butyral group, an acetal group and a formal group.

Above all, the water-insoluble polymer suitable in the present invention is a copolymer represented by the formula (1). This copolymer comprises repeating units x, y and z, and y has an acetal group.

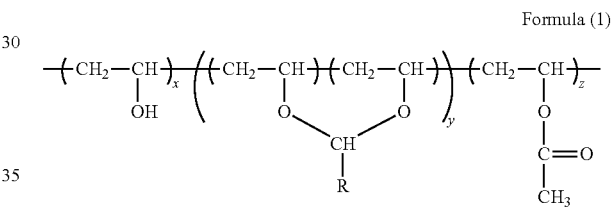

Formula (1)

In the formula (1), x, y and z are a molar ratio showing an integer of 0 or more, and x:y:z is preferably (20 to 70): (20 to 90): (1 to 10), and more preferably (30 to 60): (30 to 80): (1 to 5). R represents an alkyl group. R may be linear or branched, and is preferably a linear alkyl group having from 1 to 5 carbon atoms.

Further, the present invention is particularly preferably that the water-insoluble vinyl polymer is a polyvinyl butyral. The polyvinyl butyral used herein means that in the above formula (1), R in the y unit is a propyl group, and the y unit is 20 mol % or more.

Addition amount of the water-insoluble vinyl polymer is from 1 to 50 mass %, preferably from 1 to 30 mass %, and more preferably from 1 to 20 mass %, to the adhesive polymer.

A preferred embodiment of the multilayer analysis element for analyzing liquid samples of the present invention is described below with respect to each constituent element. In the following description, the case of employing gaseous ammonia as a gaseous substance is taken for example, and is described.

(Transparent Support)

A hydrophobic transparent support that is generally used in such an analysis element, for example, a transparent support comprising a polymer such as a polyethylene terephthalate, a polycarbonate or a polyvinyl compound, is used as the transparent support. Thickness of the transparent support is from about 50 to 1,000 µm, and generally from about 80 to 300 µm.

(Detection Layer)

The detection layer contains at least a substance that generates a detectable change by ammonia as a gaseous substance, an adhesive polymer, and a water-insoluble vinyl polymer.

As the substance that generates a detectable change by a gaseous substance, for example, a compound that generates change in absorption wavelength by reacting with gaseous ammonia (hereinafter referred to as a color precursor) is preferable. Examples of the color precursor that can be used in the analysis element of the present invention include leuco dyes such as a leucocyanine dye, a nitro-substituted leuco dye and a leucophthalene dye (described in JP-A-52-3488 and US Patent RE 30 267); pH indicators such as bromphenol blue, bromcresol green, bromthymol blue, quinoline blue and rosolic acid (described in Chemical Dictionary, Vol. 10, pages 63-65, Kyoritsu Shuppan Co., Ltd.); triarylmethane dye precursors; leucobenzilidene dyestuffs (described in JP-A-56-145273); diazonium salt and azo dye couplers; and base bleachable dyes.

When at least one of those color precursors is mixed with the adhesive polymer and the water-insoluble vinyl polymer, and the resulting mixture is applied on the transparent support, the detection layer can be formed. Further, polymers other than the polymers described above can be co-used as a binder polymer. The other binder polymers used are gelatins such as acid-treated gelatin, alkali-treated gelatin and deionized gelatin; cellulose acetates such as cellulose acetate, cellulose acetate butyrate and cellulose acetate propionate; alkyl celluloses such as methyl cellulose, ethyl cellulose and propyl cellulose; and the like.

It is suitable that the amount of the color precursor used is from about 0.1 to 50 mass %, and preferably from about 0.5 to 20 mass %, to the mass of the adhesive polymer, the water-insoluble vinyl polymer and the other binder polymer (hereinafter sometimes simply referred to as a binder polymer) Further, for the purpose of controlling sensitivity, various buffers, organic acids, inorganic acids and the like can be added to adjust pH. The buffer can be selected from the materials described hereinafter, and as the organic acid and inorganic acid, ethanesulfonic acid, aspartic acid, azelaic acid, glutaric acid, succinic acid, glutaconic acid, tartaric acid, pimelic acid, malonic acid, malic acid, 3,3-dimethylglutaric acid, citric acid, p-toluenesulfonic acid, perchloric acid, hydrochloric acid and the like can be used. Further, alkalis such as sodium hydroxide, potassium hydroxide, disodium carbonate and sodium bicarbonate can be added to the detection layer. A solvent used to form a coating liquid is suitably an organic solvent such as acetone, 2-methoxyethanol, methyl ethyl ketone or ethanol, water or mixed solvents of those. The color precursor, the binder polymer and the like are added to those solvents such that the solid concentration is from about 1 to 30 mass %, and preferably from about 3 to 20 mass %, thereby forming a coating liquid. This is applied to the transparent support in a dry thickness of from about 1 to 30 μm, and preferably from 2 to 20 μm, and dried to form the detection layer.

A liquid blocking layer is provided on the detection layer. It is preferable that the liquid blocking layer is constituted of a microporous substance having through-air holes that at the time of the production of the multilayer analysis element and/or at the time of the analytical operation, liquids such as a coating liquid and a sample liquid, and interfering components (such as an alkaline component) dissolved and contained in those liquids do not substantially permeate and a gaseous substance such as gaseous ammonia can selectively permeate.

The liquid blocking layer in the present invention comprises one layer or two layers or more of a porous film. In the case of the porous film of two layers or more, it is preferable that a hole size of the porous film as the uppermost layer contacting with a reagent layer described hereinafter is the same hole size of or smaller than that of the porous film just under the same. Specifically, the hole size of the porous layer as the uppermost layer is from 0.01 to 1 μm, and preferably from 0.04 to 0.2 μm, and the hole size of the porous film just under the same is from 0.2 to 20 μm, and preferably from 0.5 to 10 μm, and the ratio of an average hole size of the porous film as the uppermost layer/hole size of the porous film just under the same is from 0.001 to 1.0, and preferably from 0.01 to 0.5. The hole size in the present specification means an average hole size, unless otherwise indicated. Material of the porous film is not particularly limited, but a polyethylene, a polypropylene, fluorine-containing polymers such as a polytetrafluoroethylene, a cellulose acetate, a polysulfone, a polyamide (nylons), or mixtures of those are exemplified. A combination of a polyethylene porous film and a polypropylene porous film is preferable. Each porous film has a thickness of from 3 to 40 μm, and preferably from 5 to 20 μm. Two layers or more, generally 2 to 3 layers, of those films are combined to form a liquid blocking layer. It is suitable that porosity of the entire liquid shielding film is from 25 to 90%, and preferably from 35 to 90%, and the overall thickness is from 10 to 50 μm, and preferably from 10 to 30 μm.

The liquid shielding film is adhered to the detection layer with practical strength. Adhesion is conducted that surface of the detection layer is in a wet state, and the liquid film is adhered thereto and dried. The term "wet state" means that a solvent dissolving a binder remains, or a dried film is wetted with a soluble solvent, and a binder is in a swelled state, a dispersed state or a solution state.

Adhesion between the porous films is conducted with physical and/or chemical means such as adhesion in a point-to-point contact state using heat a thermocompression or hot melt adhesive. Those may successively be laminated, or porous layers may be laminated with each other, followed by adhering the resulting laminate to the detection layer.

A reagent layer can be provided on the liquid blocking layer. The reagent layer is a layer generally containing, for example, a reagent that reacts with an ammonia product to form ammonia (generally an enzyme or a reagent containing an enzyme), an alkaline buffer for efficiently liberating ammonia formed by the reaction as gaseous ammonia, and a hydrophilic polymer binder having film-formability. Examples of the combination of the ammonia formation substrate and the reagent include urea/urease, creatine/creatine deiminase, amino acid/amino acid-dehydrogenase, amino acid/amino acid oxydase, amino acid/amino acid-dehydratase, amino acid/ammonia-lyase, amine/amine-oxydase, diamine/amine-oxydase, glucose and phospho-amidate/phospho-amidate hexose phospho-transferase, ADP/kinase carbamate and carbamol phosphate, acid amide/amidohydrolase, nulcleo base/deaminase, nucleoside/deaminase, nucleotide/deaminase, and guanine/quanaze.

The alkaline buffer that can be used in the reagent layer is a buffer having pH in a range of from 7.0 to 10.5, and preferably from 7.5 to 10.0. Examples of the buffer include Good's buffers such as ethylenediamine tetraacetate (EDTA), tris(hydroxymethyl)aminomethane (Tris), phosphate buffer, N,N-bis(2-hydroxyethyl)glycine (Bicine), N-2-hydroxyethylpiperadine-N'-2-hydroxypropane-3-sulfonic acid (HEPSO), and N-hydroxyethylpiperadine-N'-ethanesulfonic acid (HEPES); and borate buffers.

Examples of the hydrophilic polymer binder having film-formability that can be used in the reagent layer include gelatin, agarose, polyvinyl alcohol, polyacrylamide, hydroxymethyl cellulose, hydroxyethyl cellulose, and polyvinyl pyrrolidone.

Other than the reagent that reacts with an ammonia product to form ammonia, the alkaline buffer for efficiently liberating ammonia formed by the reaction as gaseous ammonia, and the hydrophilic polymer binder having film-formability, the reagent layer can contain a wetting agent, a binder crosslinking agent (a curing agent), a stabilizer, a heavy metal ion trapping agent (a complexing agent) and the like according to need.

The reagent layer can be formed by mixing the reagent that reacts with an ammonia formation substrate to form ammonia, the alkaline buffer for efficiently liberating ammonia formed by the reaction as gaseous ammonia, and the above reagents added according to need with the hydrophilic polymer binder having film-formability such as gelatin to prepare a coating liquid, and applying the coating liquid on the liquid blocking layer, followed by drying.

It is suitable that the amount of the reagent that reacts with an ammonia formation substrate to form ammonia, contained in the reagent layer is in a range of generally from about 0.1 to about 50 mass %, and preferably from about 0.2 to about 20 mass %, based on the mass of the binder. It is suitable that the amount of the alkaline buffer is in a range of from about 0.1 to about 60 mass % based on the mass of the binder. The dry film thickness of the reagent layer is in a range of generally from about 1 to about 40 μm, and preferably from about 2 to about 20 μm.

A spreading layer is provided on the reagent layer. As the spreading layer, there are fibrous microporous spreading layers such as woven fabric spreading layers (for example, plain weave fabrics such as broadcloth and poplin) as described in, for example, JP-A-55-164356 (corresponding to U.S. Pat. No. 4,292,272) and JP-A-57-66359 (corresponding to U.S. Pat. No. 4,783,315), knitted fabric spreading layers (for example, tricot stitch fabric, double tricot stitch fabric and Milanese stitch fabric) as described in, for example, JP-A-60-222769 (corresponding to EP 0 162 302A), organic polymer fiber pulp-containing papermaking paper spreading layers as described in JP-A-57-148250, and spreading layers formed by coating a dispersion containing fibers and a hydrophilic polymer as described in JP-A-57-125847; non-fibrous isotropically microporous spreading layers such as membrane filter layers (brushed polymer layer) as described in, for example, JP-B-53-21677 (corresponding to U.S. Pat. No. 3,992,158), continuous micropore-containing isotropically microporous spreading layers in which fine particles such as polymer microbeads are adhered to a hydrophilic polymer binder in point-to-point contact state, and continuous micropore-containing isotropically microporous layer (three dimensional lattice particulate structure layer) spreading layers in which polymer microbeads are adhered with a polymer adhesive that does not swell with water in point-to-point contact state as described in JP-A-55-90859 (corresponding to U.S. Pat. No. 4,258,001); and spreading layers having excellent blood cell separability in which plural microporous layers (for example, two layers of a woven fabric or a knitted fabric and a membrane filter, and three layers of a woven fabric or a knitted fabric, a membrane filter, and a woven fabric or a knitted fabric) are adhesion laminated on their surfaces with an adhesive in a fine discontinuous point state or an island state (dot state in printing field) as described in, for example, JP-A-61-4959 (corresponding to U.S. Pat. No. 5,019,347), JP-A-62-138756, JP-A-62-138757 and JP-A-62-138758 (corresponding to EP 0 226 465A).

The woven fabric or knitted fabric used in the spreading layer can be hydrophilicized by subjecting at least one surface thereof to physical activation treatment represented by glow discharge treatment or corona discharge treatment as described in JP-A-57-66359, or conducting hydrophilicization treatment such as water washing defatting treatment or hydrophilic polymer impregnation as described in, for example, JP-A-55-164356 and JP-A-57-66359 or successively conducting those treatment steps in an appropriate combination, thereby increasing adhesive force to the layer at the lower side (side near the support). Further, spread area or spreading of the liquid sample can be controlled by applying a polymer-containing aqueous solution or a polymer-containing water/organic solvent mixed solution from the upper side of the spreading layer as described in, for example, JP-A-59-171864, JP-A-60-222769 and JP-A-60-222770.

Further, where the analysis element of the present invention is used as creatine determination, an ammonia diffusion prevention layer and an endogenous ammonia supplemental layer can be provided in this order between the reagent layer and the spreading layer. The ammonia diffusion prevention layer and the endogenous ammonia supplemental layer are described in, for example, JP-A-4-157364 and are conventional. However, for example, the ammonia diffusion prevention layer is a layer that supplementation of ammonia and ammonia formation reaction are not substantially conducted, and can be formed using a hydrophilic polymer such as hydroxypropyl cellulose. Thickness of the ammonia diffusion prevention layer is, for example, from 2 to 50 μm. The endogenous ammonia supplemental layer is a layer containing a reagent that acts to endogenous ammonia already present in the liquid sample and changes the same into a state that does not substantially reach the reagent layer. The reagent includes a composition containing an enzyme having catalystic ability that changes ammonia into other substance as a substrate. Specific example of the composition is a composition containing a hydrophilic polymer such as hydroxyethyl cellulose as a binder polymer, α-ketoglutaric acid, NADPA, and glutaminate dehydrogenase. Thickness of the endogenous ammonia supplemental layer is, for example, from 1 to 30 μm.

Further, a color shielding layer and a light reflection layer can be provided between the reagent layer and the spreading layer. The color shielding layer or the light reflection layer is a layer that white fine particles having both light shielding properties and light reflection properties, such as titanium dioxide fine particles and barium sulfate fine particles, are nearly uniformly dispersed in the hydrophilic polymer binder such as gelatin, and its dry thickness is in a range of from about 2 μm to about 20 μm.

Further, the conventional adhesive layer comprising a hydrophilic polymer can be provided on the reagent layer, the ammonia diffusion prevention layer, the endogenous ammonia supplemental layer, the color shielding layer or the light reflection layer for the purpose of strongly adhering and integrating. Dry thickness of the adhesive layer is in a range of from about 0.5 μm to about 5 μm.

A surfactant can be contained in the reagent layer, the ammonia diffusion prevention layer, the endogenous ammonia supplemental layer, the color shielding layer or the light reflection layer, the adhesive layer, the spreading layer and the like. Example of the surfactant is a nonionic surfactant. Specific examples of the nonionic surfactant include p-octylphenoxypolyethoxyethanol, p-nonylphenoxypolyethoxyethanol, polyoxyethylene oleyl ether, polyoxyethylene sorbitan monolaurate, p-nonylphenoxypolyglycidol and octyl glucoside. By containing the nonionic surfactant in the spreading layer, spreading action (metering action) of an aqueous liquid sample becomes better. By containing the nonionic surfactant in the reagent layer, the ammonia diffusion prevention layer, the endogenous ammonia supplemental layer, the color shielding layer or the light reflection layer, the adhesive layer, and the like, water in the aqueous liquid sample is liable to be substantially uniformly absorbed in the reagent layer at the time of analytical operation, and further, liquid contact with the spreading layer becomes rapid and substantially uniform.

To measure, for example, ammonia or ammonia formation substrate in the liquid sample using the analysis element of the present invention, aqueous liquid sample droplets of whole blood, blood plasma, blood serum, urine and the like in a range of from 3 to 30 μL, and preferably from 6 to 15 μL, are dropped on the spreading layer, and after conducting incubation at substantially constant temperature in a range of from about 20 to 40° C. in a range of from 1 to 10 minutes, the degree of color change (coloration or decoloration) of the detection layer is measured by reflection photometry from the transparent support side, or is visually compared with the standard color.

Example 1

The present invention is further described by the Example and the Comparative Example, but the invention is not limited to the following examples.

Example 1

A detection layer was applied to a transparent polyethylene terephthalate (PET) film having a thickness of 180 μm by an ethanol solution so as to be the following coverage and dried.

| Detection layer | |
|---|---|
| Bromphenol blue | 110 mg/m$^2$ |
| Polyvinyl methyl ether | 1.8 g/m$^2$, mass average molecular weight: about 40,000 |
| Polyvinyl butyral | 0.18 g/m$^2$, average degree of polymerization: about 300 |
| Sodium hydroxide | 6.8 mg/m$^2$ |

Next, a polyethylene-made membrane filter having an average pore size of 0.2 μm, a porosity of 75% and a thickness of 100 μm was uniformly press-bonded on the detection layer to provide a liquid blocking layer. A reagent layer was applied to the liquid blocking layer from an aqueous solution so as to be the following coverage and dried.

| Reagent layer (pH 9.0) | |
|---|---|
| Hydroxyethyl cellulose | 3.0 g/m$^2$ |
| Average molecular weight: | about 40,000 |
| Average degree of substitution of hydroxyethyl group: | DS = 1.0 to 1.3 |
| Average value of mole number: | MS = 1.8 to 2.5 |
| Sodium tetraborate | 1 g/m$^2$ |
| Creatine iminohydrase (EC 3.5.4.21) | 1,800 U/m$^2$ |

Further, an ammonia diffusion prevention layer was applied to the reagent layer so as to be the following coverage and dried.

| Ammonia diffusion prevention layer | |
|---|---|
| Hydroxypropyl cellulose | 20.0 g/m$^2$ |
| Methoxy group | 28 to 30% |
| Hydroxypropoxy group | 7 to 12% |

Viscosity of 2% aqueous solution at 20° C. 0.05 Pas (50 cps)

Further, an endogenous ammonia supplemental layer was applied to the ammonium diffusion prevention layer so as to be the following coverage and dried.

| Endogenous ammonia supplemental layer (pH 8.2) | |
|---|---|
| Hydroxyethyl cellulose | 5 g/m$^2$ |
| Ampholyte | 1.2 g/m$^2$ |
| α-Ketoglutaric acid | 1.2 g/m$^2$ |
| NADPH | 0.4 g/m$^2$ |
| Glutamate dehydrogenase (EC 1.4.1.4) | 1,000 U/m$^2$ |

The above endogenous ammonia supplemental layer was nearly uniformly wetted with 0.2% P-nonylphenoxypolyglycidol aqueous solution, and immediately a polyester knitted fabric (gauge number 40) was uniformly press bonded thereon. Further, an ethanol solution of a polyvinylpyrrolidone was impregnation applied to the laminate so as to be the following coverage and dried for the purpose of improving spreadability, and slit into 12 mm width to prepare an integral multilayer analysis element for creatine quantitative determination.

Polyvinyl pyrrolidone 7.5 g/m$^2$, average molecular weight: about 1,200,000

Comparative Example 1

An integral multilayer analysis element for creatine quantitative determination was prepared in the same manner as in Example 1, except that the detection layer was prepared without using polyvinyl butyral.

Peel force between the support transparent PET film and the detection layer in the integral multilayer analysis element for creatine quantitative determination obtained above was measured. The peel force is a value measured by the following method.

Peel force measurement method: TENSILON UTM-II-20, a product of Orientech Co., is used as a peel force measurement device. A sample is cut into a strip shape having a width of 12 mm and a length of 150 mm, and a PET film surface thereof is adhered to a mount with a double-sided adhesive tape. Interface between the PET film and the detection layer is manually peeled off, the peeled detection layer is held with a clip and connected to a measurement device, and measurement is initiated. Peel force is recorded on a graph as a recorder, and peel force can be read from the graph.

Further, simultaneously, sensitivity and storage performance of the sample were measured.

The sensitivity was measured such that 10 μl of a solution containing creatine in a proportion of 12.7 mg/dl was dropped on the spreading layer, and color optical density (OD) after 5 minutes was measured with measurement wavelength of 650 nm, and was shown as a relative value.

The storage performance was examined by conducting an acceleration test at 45° C. for 4 days. The evaluation is A:within ±0.5% and B:larger than ±0.5%.

The results are shown below.

|  | Peel force | Sensitivity | Storage Performance |
|---|---|---|---|
| Example 1 | 218 g | 104% | A |
| Comparative Example 1 | 15 g | 100% | A |

It is seen that in the analysis element of Example 1, peel force is about 15 times as compared with the conventional analysis element that does not use a water-insoluble vinyl polymer (Comparative Example 1), deterioration of sensitivity is not generated, and storage stability is good.

The invention claimed is:

1. A multilayer analysis element for analyzing liquid samples, which comprises a transparent support having at least:
   a detection layer containing a substance that generates a detectable change by a gaseous substance;
   a liquid blocking layer that selectively permeates the gaseous substance; and a spreading layer, integrally adhesion laminated thereon in this order,
   wherein the detection layer is comprised of a polyvinyl methyl ether and a polyvinyl butyral in order to bind the detection layer to the transparent support;
   wherein the amount of the polyvinyl butyral is from 1 to 30 mass % to polyvinyl methyl ether; and
   wherein the polyvinyl methyl ether and a polyvinyl butyral of the detection layer are mixed together with the substance that generates a detectable change by a gaseous substance.

* * * * *